United States Patent
Wang et al.

(10) Patent No.: US 8,500,828 B2
(45) Date of Patent: Aug. 6, 2013

(54) PROCESS FOR PREPARING A BIO-DIESEL

(75) Inventors: Haijing Wang, Beijing (CN); Zexue Du, Beijing (CN); Enze Min, Beijing (CN); Guoqiang Gao, Beijing (CN)

(73) Assignees: China Petroleum & Chemical Corporation, Beijing (CN); Research Institute of Petroleum Processing, Sinopec, Beijing (CN)

( * ) Notice: Subject to any disclaimer, the term of this patent is extended or adjusted under 35 U.S.C. 154(b) by 699 days.

(21) Appl. No.: 12/519,326

(22) PCT Filed: Dec. 15, 2006

(86) PCT No.: PCT/CN2006/003430
§ 371 (c)(1),
(2), (4) Date: Jul. 28, 2009

(87) PCT Pub. No.: WO2008/071041
PCT Pub. Date: Jun. 19, 2008

(65) Prior Publication Data
US 2010/0024285 A1  Feb. 4, 2010

(51) Int. Cl.
*C10L 1/19* (2006.01)
(52) U.S. Cl.
USPC .................................. 44/388; 44/307; 44/308
(58) Field of Classification Search
USPC ..................... 554/170, 167; 210/641; 44/388
See application file for complete search history.

(56) References Cited

U.S. PATENT DOCUMENTS

| | | | |
|---|---|---|---|
| 4,652,406 A | 3/1987 | Lepper et al. | |
| 4,668,439 A * | 5/1987 | Billenstein et al. | 554/167 |
| 5,017,291 A * | 5/1991 | Semler et al. | 210/641 |
| 5,525,126 A | 6/1996 | Basu et al. | |
| 6,090,959 A | 7/2000 | Hirano et al. | |
| 6,812,359 B2 * | 11/2004 | Goto et al. | 554/170 |
| 6,818,026 B2 | 11/2004 | Tateno et al. | |
| 2004/0087809 A1 | 5/2004 | Nakayama et al. | |
| 2008/0051592 A1 * | 2/2008 | McNeff et al. | 554/170 |

FOREIGN PATENT DOCUMENTS

| | | | |
|---|---|---|---|
| CN | 1152885 A | | 6/1997 |
| CN | 1247221 A | | 3/2000 |
| CN | 1287572 A | | 3/2001 |
| CN | 1111591 C | | 6/2003 |
| CN | 1472280 A | | 2/2004 |
| CN | 1473907 A | | 2/2004 |
| CN | 1142993 C | | 3/2004 |
| CN | 1664072 A | | 9/2005 |
| CN | 1786117 | * | 6/2006 |
| CN | 1786117 | | 6/2006 |
| CN | 1810932 A | | 8/2006 |
| DE | 3444893 A1 | | 6/1986 |
| EP | 0985654 A1 | | 3/2000 |
| EP | 1477551 A1 | | 11/2004 |
| EP | 1 061 120 B1 | | 6/2006 |
| JP | 2000108379 A | | 4/2000 |
| JP | 2006188590 A | | 7/2006 |
| WO | WO9601199 | | 1/1996 |

OTHER PUBLICATIONS

An, Wen-jie, "Preparation of Biodiesel by Supercritical Method", China University of Mining and Technology, 2006, pp. 20-23 With English Language Abstract.
Sun Shiyao, "Progress in Production of Biodiesel in Supercritical Methanol", Jingzi Shiyou Huagong (2006), 23 (1) 53-56 with English Language Abstract.

* cited by examiner

*Primary Examiner* — James Goloboy
*Assistant Examiner* — Chantel Graham
(74) *Attorney, Agent, or Firm* — Scully, Scott, Murphy & Presser, P.C.

(57) ABSTRACT

The present invention relates to a process for preparing a bio-diesel, comprising the steps of, in the presence of an additional free fatty acid source, reacting a raw oil-fat with $C_1$-$C_6$ monohydric alcohol in a reactor, and separating fatty acid esters from the reacted materials, so as to produce the bio-diesel, wherein the amount of the free fatty acid in the free fatty acid source ranges from 2-100 wt % and is higher than the amount of the free fatty acid in the raw fat-oil. The present process can increase the fatty acid ester yield and purity of raw oil-fats having a low reaction activity, and has a high adaptability to raw materials.

37 Claims, No Drawings

PROCESS FOR PREPARING A BIO-DIESEL

TECHNICAL FIELD

The present invention relates to a process for preparing a bio-diesel by reacting an oil-fat with a monohydric alcohol.

BACKGROUND OF THE INVENTION

Bio-diesel may be prepared by transesterification of an oil-fat with a monohydric alcohol. Besides fatty acid esters, the products of the transesterification may include monoglycerides, diglycerides, glycerol by-products, as well as the unreacted alcohols and crude oil-fat. Bio-diesel primarily comprises fatty acid esters, and possibly other trace substances such as monoglycerides, diglycerides, glycerol and the like. In the prior art, there are the acid catalysis method, base catalysis method, enzyme catalysis method and supercritical method for the preparation of bio-diesel.

CN1473907A discloses using as raw materials the heels from the refining of vegetable oils and the edible recovered oil, carrying out the production procedures comprising removing impurities by acidification, continuously dehydrating, esterifying, stratifying, and distilling under reduced pressure, and the catalyst used in the process is formed by complex formulation of inorganic and organic acids such as sulfuric acid, hydrochloric acid, p-toluene sulfonic acid, dodecylbenzene sulfonic acid, naphthalene sulfonic acid and the like. The continuous vacuum dehydration is carried out to a water content of less than 0.2% at a pressure of 0.08-0.09 MPa and a temperature of 60-95° C. Additionally, the catalyst is added in an amount of 1-3% in the esterification step; the esterification temperature ranges from 60-80° C.; and the reaction lasts 6 hours. After reaction, the product is neutralized to remove the catalyst, then stratified to remove water, and distilled under reduced pressure to obtain a bio-diesel. The problems of said acid catalysis include slow reaction rate, massive spent acids, and environmental pollution.

DE3444893 discloses a process, wherein an inorganic acid is used as the catalyst; free fatty acids and alcohols are esterified at normal pressure and a temperature of from 50-120° C.; oils are pre-esterified and transesterified in the presence of an alkali metal catalyst. However, the residual inorganic acid catalyst will be neutralized with the alkali, so as to increase the amount of the alkali metal catalyst. Moreover, the pre-esterification will lengthen the processing process, increase the equipment investment, greatly enhance the energy consumption and incur a great loss of the materials. Moreover, the basic catalyst needs to be removed from the product, and a great deal of waste water will be produced.

CN1472280A discloses a process for preparing a bio-diesel, wherein fatty acid esters are used as the acyl receptor, and organisms are catalyzed for interesterification in the presence of a bio-enzyme. However, the presence of an enzyme catalyst has the disadvantages of long reaction time, low efficiency, high enzyme price, and a high possibility of inactivation in high purity methanol.

CN1142993C discloses a process for preparing fatty acid esters by using an oil-fat and alcohol in the absence of a catalyst and under the condition that either of said oil-fat and alcohol is in a supercritical state. The process is carried out using a batch kettle reaction, and is unfavorable to a large industry-scale production CN1111591C discloses a process for preparing fatty acid esters by continuously reacting an oil-fat with a monohydric alcohol at a temperature of 270 to 280° C. and a pressure of 11-12 Mpa in a tubular reactor. However, the yield of fatty acid methyl ester is only 55-60%.

From the prior art above, it can be found that there are the problems of lower yield of bio-diesel and lower raw material processing capacity in the preparation of a bio-diesel by medium and high pressure methods.

SUMMARY OF THE INVENTION

The present invention relates to a process for preparing a bio-diesel, comprising the steps of, in the presence of an additional free fatty acid source, reacting a raw oil-fat with $C_1$-$C_6$ monohydric alcohol in a reactor, and separating fatty acid esters from the reacted materials, so as to produce the bio-diesel, wherein the amount of the free fatty acid in the free fatty acid source ranges from 2-100 wt % and is higher than the amount of the free fatty acid in the raw fat-oil. Said process can improve the bio-diesel yield.

DETAILED DESCRIPTION OF THE INVENTION

The present invention relates to a process for preparing a bio-diesel, comprising the steps of, in the presence of an additional free fatty acid source, reacting a raw oil-fat with $C_1$-$C_6$ monohydric alcohol in a reactor, and separating fatty acid esters from the reacted materials, so as to produce the bio-diesel, wherein the amount of the free fatty acid in the free fatty acid source ranges from 2-100 wt % and is higher than the amount of the free fatty acid in the raw fat-oil.

Said term oil-fat mentioned in, for example, the expression "a raw oil-fat" and "an oil-fat having a high acid number (or high acid number oil-fat)" is generally known in the art and is a general designation of oils and fats. The primary components thereof are fatty acid triglycerides. Generally, an oil-fat in a liquid state at normal temperature is termed as oil, and an oil-fat in a solid or semi-solid state at normal temperature is termed as fat. Said oil-fat comprises vegetable oils and animal oils, and further oils from microorganisms, algae and the like, and even crude oils, waste oil-fat and degenerative oil-fat, and the like, wherein said crude oils are the oil-fat which is not refined or fails to satisfy the product standard after refinement. The refining process includes, but is not limited to, degumming, alkali refining, dephosphoration, decolorization, deodorization and the like. The oil-fat may also comprise unsaponifiable matters in a relatively high content. Examples of vegetable oils comprise, but are not limited to, soybean oil, rapeseed oil, peanut oil, sunflower seed oil, palm oil, cocoanut oil, and aliphatic group-containing substances from fruits, stems, leaves, limbs and roots derived from various agricultural crops and wild plants (including a tall oil produced during the paper making). Examples of animal oil-fat include, but are not limited to, lard oil, beef tallow, mutton tallow, fish oil and the like. Said oil-fat may be the mixture of two or more oil-fats.

The amount of the free fatty acid in said raw oil-fat is less than 50 wt %, preferably less than 30 wt %, more preferably less than 20 wt %. In one embodiment, the raw oil-fat comprises palm oil. In another embodiment, the raw oil-fat is a waste oil-fat.

Said $C_1$-$C_6$ monohydric alcohol is a monohydric fatty alcohol having from 1 to 6 carbon atoms, which may be a saturated or unsaturated alcohol. Examples of the monohydric alcohol include, but are not limited to, methanol, ethanol, n-propanol, isopropanol, allyl alcohol, butanol such as n-butanol, isobutanol, amyl alcohol such as n-amyl alcohol and the like. A single alcohol, or a mixture of two or more alcohols may be used. Said monohydric alcohol is preferably selected from methanol and ethanol, especially methanol. The molar ratio of $C_1$-$C_6$ monohydric alcohol to the raw oil-fat may range from 3 to 60:1, preferably from 4 to 12:1.

Said free fatty acid source can be a free fatty acid which may be saturated or unsaturated, preferably $C_{10}$-$C_{24}$ saturated or unsaturated fatty acid, more preferably $C_{12}$-$C_{18}$ unsaturated fatty acid which may has one or more double-bonds, preferably one double-bond. Examples of the free fatty acid comprise, but not limited to, tetracosanoic acid, docosanoic acid, eicosanic acid, nonadecanoic acid, stearic acid, heptadecoic acid, palmitic acid, pentadecanoic acid, myristic acid, tridecanoic acid, lauric acid, undecanoic acid, decanoic acid, docosenoic acid, arachidonic acid, oleic acid, linolenic acid, linoleic acid, undecenoic acid, etc. A specially preferred free fatty acid is oleic acid. Said free fatty acid is present in an amount of 1-50 wt %, preferably 2-40 wt %, relative to the weight of the raw oil-fat.

Said free fatty acid source can also be the oil-fat having a high acid number, for example crude oil, waste oil-fat, or the like. The amount of the free fatty acid in the oil-fat having a high acid number is more than 2 wt %, preferably 5 to <100 wt %, more preferably 10 to 60 wt %, and higher than the amount of the free fatty acid in the raw oil-fat. The weight ratio between the raw oil-fat and the oil-fat having a high acid number ranges from 1:0.02 to 50, preferably 1:0.04 to 20, more preferably 1:0.06 to 10. The category of the oil-fat having a high acid number can be same or different from that of the raw oil-fat.

The reaction between the raw oil-fat and $C_1$-$C_6$ monohydric alcohol in the presence of an additional free fatty acid source can be optionally carried out under the condition that an alkaline compound is used as a catalyst. Said alkaline compound can be selected from, e.g. hydroxides, alcoholates, oxides, carbonates, bicarbonates and aliphatic carboxylate of the Groups IA and IIA elements in the periodic table, preferably hydroxides, alcoholates, oxides, carbonates, bicarbonates and $C_{12}$-$C_{24}$ fatty acid salts of sodium, potassium, magnesium, calcium and barium, more preferably hydroxides, oxides, alcoholates and $C_{12}$-$C_{24}$ fatty acid salts of sodium and potassium. Said alkaline compound is added in an amount of 0.005-0.3 wt %, preferably 0.008-0.2 wt %, relative to the weight of the oil-fat.

In the process of the present invention, a tubular reactor may be used. The reactor may be provided with the oil-fat and alcohols separately or after being pre-mixed. The materials may be preheated by a pre-heater before being fed into the reactor, or directly fed into the reactor. If the materials are directly fed into the reactor, the reaction functions as both a pre-heater and a reactor. If a pre-heater is used, the oil-fat and alcohol may be pre-heated respectively or pre-heated together after they are mixed. The reaction temperature ranges from 200 to 320° C., especially from 230 to 280° C.; the reaction pressure ranges from 5 to 12 MPa, especially from 6 to 10 MPa, and a relatively low pressure (e.g. 5 to 7.5 MPa) can also achieve the objective of the present invention; the liquid hourly space velocity of the oils ranges from 0.1 to 10 $h^{-1}$, especially from 0.5 to 6 $h^{-1}$, more especially from 1 to 3 $h^{-1}$. Said oils comprise the raw oil-fat and additional free fatty acid source.

In the process of the present invention, the separation of fatty acid esters comprises the steps of
  (A) separating the mixed ester phase and the glycerol phase formed in the reacted materials, and subsequently evaporating monohydric alcohols respectively from said mixed ester phase and optionally from the glycerol phase, or evaporating monohydric alcohols from the reacted materials before separating the mixed ester phase and the glycerol phase formed in the reacted materials; and
  (B) distilling or rectifying the mixed ester phase processed in step (A), or water-washing the mixed ester phase processed in step (A) and separating the ester phase formed after washing from the aqueous phase and collecting said ester phase, to obtain high purity fatty acid esters, and optionally distilling the glycerol phase processed in step (A) to obtain glycerol.

In step (A) above, monohydric alcohols may be evaporated by rectification or flash distillation under the condition that the temperature at the column bottom is less than 150° C., and the pressure may be normal pressure, vacuum, or greater than one atmospheric pressure.

In step (A) above, the mixed ester phase and glycerol phase may be separated by deposition or via a fiber bundle separator. Rapid separation via a fiber bundle separator is preferred. Said fiber bundle separator consists of a separating cylinder and a receiving tank, wherein the separating cylinder is furnished with fiber bundles consisting of stainless steel wires. The mixture of the mixed ester phase and the glycerol phase firstly passes through the separating cylinder and then is fed into the receiving tank for stratification, so as to achieve the separation of the mixture. The separation is carried out at a temperature of from 20 to 200° C., preferably from 40 to 100° C., at a pressure of greater than one atmospheric pressure or at normal pressure, e.g. from 0.1 to 0.5 MPa, preferably from 0.1 to 0.3 MPa, and at a space velocity of from 0.1 to 25 $h^{-1}$, especially from 1 to 10 $h^{-1}$, more preferably from 1 to 5 $h^{-1}$. In order to achieve better phase separation effect, the reacted materials which are heavily emulsified generally need to stand overnight if the deposition method is used. A fiber bundle separator can achieve a good separation effect in a very short time, so as to greatly enhance the separation rate and production efficiency.

In one embodiment of step (B) above, the mixed ester phase processed in step (A) above is distilled or rectified to obtain high purity fatty acid esters, wherein the distillation or rectification of said mixed ester phase may be carried out in a rectification column under reduced pressure or via a film evaporator. The mixed ester phase obtained in step (A) is fed into the reduced pressure rectification column, wherein the column bottom pressure is less than 0.1 MPa, preferably less than 0.01 MPa, more preferably less than 0.001 MPa; reflux may not occur, or the reflux ratio is controlled to range from 0.01 to 10:1, preferably from 0.1 to 2:1. The temperature of the column bottom or film evaporator ranges from 100 to 300° C., preferably from 170 to 280° C., more preferably from 190 to 280° C. The optional distillation of the glycerol phase may be similarly carried out by rectification in a reduced pressure rectification column or via a film evaporator.

In another embodiment of step (B) above, the mixed ester phase processed in step (A) above is washed by water, and the ester phase formed after washing is separated from the aqueous phase and collected to obtain high purity fatty acid esters. The water to be added during the washing is from 10 to 100 wt %, preferably from 20 to 80 wt % relative to the amount of the mixed ester phase; the temperature of water ranges from 25 to 100° C., preferably from 40 to 80° C. Washing may be carried out once or more times. If the ester phase obtained in step (B) has a relatively high acid number, an alkaline substance may be added into washing water. One or more alkaline substances selected from the group consisting of sodium carbonate, sodium bicarbonate, potassium carbonate, potassium bicarbonate, sodium hydroxide and potassium hydroxide may be added in the form of an aqueous solution for alkaline washing, wherein the alkaline substance in the aqueous solution is in a concentration of from 5 to 40 wt %, preferably from 5 to 20 wt %. The washed mixture may be re-separated into the ester phase and the aqueous phase by e.g. deposition, preferably via a fiber bundle separator, at a temperature of from 20 to 150° C., preferably from 40 to 100° C., at a pressure of greater than one atmospheric pressure or at normal pressure, and at a space velocity of from 0.1 to 25 $h^{-1}$, especially from 1 to 10 $h^{-1}$, more preferably from 1 to 5 $h^{-1}$.

The process of the present invention may further comprise step (C): separating monoglycerides and diglycerides from the mixed ester phase residues (i.e. residual liquid in the column bottom) distilled or rectified in step (B) by using a secondary molecular rectification, or evaporating monoglycerides and diglycerides from the mixed ester phase residues distilled or rectified in step (B) by using a primary molecular rectification. The evaporated monoglycerides and/or diglycerides may be recycled as required to the reactor inlet for a second reaction. More specifically, if the fraction having a higher monoglyceride content is desired, a secondary molecular rectification may be used. The residual liquid obtained from step (B) in the column bottom is fed into the molecular rectification device. The monoglyceride fraction in a higher content may be obtained at a pressure of less than 5 Pa, preferably less than 3 Pa, more preferably less than or equal to 1 Pa, and at a heating surface temperature of from 170 to 220° C., preferably 180 to 200° C. The fraction having a higher monoglyceride content may be used as an oil lubricating additive, and the heavy fractions may be fed into the secondary molecular rectification. At the pressure above and at a heating surface temperature of from 200 to 290° C., preferably 220 to 250° C., diglycerides having a higher purity may be obtained. These monoglycerides and diglycerides can be recycled as raw materials to the reactor inlet for second reaction. If the monoglyceride fraction in a higher content is not necessary, monoglycerides and diglycerides may be directly evaporated by using a primary molecular rectification, and then recycled to the reactor inlet for second reaction. In addition, the heavy residue may be used as fuel. In order to achieve the object of separating more components, the continuous multistage (or multi-group) operation may be used for the molecular rectification.

According to the present process, the biodiesel yield of the raw oil-fat having a low reaction activity is increased, the defect that the product obtained from the high acid number raw oil-fat has a high acid number is avoided, and the biodiesel yield resulting from the mixed oils as raw materials are significantly higher than the sum of the yields resulting from the respective low activity oils and high acid number oil-fat when they are reacted alone. High purity of the fatty acid ester can also be achieved together with a strong raw material-processing capability, and thus the inventive process makes merit in industry applications. The process of the present invention has a strong adaptability to raw materials. Even if the oil-fat has a very high acid number or even contains non-saponifiable matters in a higher content, it can be directly processed without the multifarious pretreatment so as to reduce the energy consumption and equipment investment. In addition, the process of the present invention may effectively separate monoglycerides, diglycerides and organic matters in non-refined oils having a relatively high boiling point, and may enable the components in non-refined oils which can become fatty acid methyl esters to be utilized to a maximum extent.

The present process is easy to be carried out, has substantially no liquid, gas, and solid waste, and is environmentally friendly.

EXAMPLES

The following examples are used to further explain the present invention, but the present invention is not limited to these examples. The raw materials used below are commercially available or easily produced according to the common technology in the art.

The bio-diesel yield stated in the examples can be calculated from the ratio of the bio-diesel weight to the weight sum of the raw oil-fat and free fatty acid source; the purity of fatty acid methyl ester can be calculated from the ratio of the fatty acid methyl ester weight to the bio-diesel weight.

Comparison Example 1

A refined soybean oil having 0.7 wt % of free fatty acid was continuously fed as raw materials into a tubular reactor at an oil liquid hourly space velocity of 1.2 $h^{-1}$ and methanol:oil molar ratio of 5. The reaction temperature was 280° C. and the pressure was 9.5 MPa. Methanol and glycerol were separated from the raw product of reaction, which then was vacuum-rectified to evaporate the bio-diesel. The yield of the bio-diesel was 47 wt %.

Comparison Example 2

A rapeseed oil having 0.45 wt % of free acid was continuously fed as raw materials into a tubular reactor at an oil liquid hourly space velocity of 1.2 $h^{-1}$ and methanol:oil molar ratio of 7. The reaction temperature was 272° C. and the pressure was 8 MPa. Methanol and glycerol were separated from the raw product of reaction, which then was vacuum-rectified to evaporate the bio-diesel. The yield of the bio-diesel was 61 wt %.

Example 1

A crude soybean oil having 1.2 wt % non-saponifiable matters and 36 wt % free fatty acid was mixed with the rapeseed oil in comparison example 2 in a mixing ratio of 0.3:1. The mixture was continuously fed into a tubular reactor at an oil liquid hourly space velocity of 1.2 $h^{-1}$ and methanol:oil molar ratio of 7. The reaction temperature was 272° C. and the pressure was 8 MPa. Methanol and glycerol were separated from the raw product of reaction, which then was vacuum-rectified to evaporate the bio-diesel. The yield of the bio-diesel was 92.2 wt %, and the acid number of the bio-diesel was 3.5 mgKOH/g, wherein the fatty acid methyl ester had a purity of 98 wt %. The residual liquid in the column bottom could be recycled as raw material to the reactor inlet for a second reaction. The components in the raw materials which could become fatty acid methyl esters were almost converted to the desired product.

Under the same conditions, above crude soybean oil having 36 wt % free fatty acid was used as raw materials, and a bio-diesel was produced in a yield of 87.2 wt % and had an acid number of 9.0 mgKOH/g.

Example 2

A cotton seed oil having 1.5 wt % non-saponifiable matters and 26 wt % free fatty acid was mixed with the refined soybean oil in comparison example 1 in a mixing ratio of 1:1. The mixture was fed into a tubular reactor at an oil liquid hourly space velocity of 1.2 $h^{-1}$ and methanol:oil molar ratio of 5. The reaction temperature was 272° C. and the pressure was 8.5 MPa. Methanol and glycerol were separated from the raw product of reaction, which then was vacuum-rectified to evaporate the bio-diesel. The yield of the bio-diesel was 91 wt %, and the acid number of the bio-diesel was 3.3 mgKOH/g, wherein the fatty acid methyl ester had a purity of 97.5 wt %, and the free glycerol content was 0.2 wt %. To the ester phase, 5% sodium carbonate solution at 40° C. was added for washing. The washed mixture was fed into a fiber bundle separator at a temperature of 40° C. and a liquid hourly space velocity of 10 $h^{-1}$. The ester phase and the aqueous phase were separated. The acid number of the ester phase was 0.27 mgKOH/g and the content of the free glycerol was 0.018 wt %. The residual liquid in the column bottom could be recycled as raw material to the reactor inlet for a second reaction.

Under the same conditions, above cotton seed oil having 26 wt % free fatty acid was used as raw materials, and a bio-diesel was produced in a yield of 86 wt % and had an acid number of 7.2 mgKOH/g.

Example 3

A waste fat-oil having 14.3 wt % free fatty acid was mixed with a soybean oil and rapeseed oil in a mixing ratio of 1:1:1. The mixture was continuously fed into a tubular reactor at an oil liquid hourly space velocity of 1.2 $h^{-1}$ and methanol:oil molar ratio of 5. The fatty acid methyl ester was produced under a reaction temperature of 320° C. and a pressure of 9 MPa. The crude product flowing out from the reactor was then fed into a flash column to remove methanol at a temperature of less than 150° C., and recycle and reuse the methanol. The residual materials were fed into a separator comprising fiber bundles, and an ester phase was separated out at a temperature of 52° C. and a liquid hourly space velocity of 5 $h^{-1}$, and the ester phase was fed into a vacuum rectification column. The bio-diesel was obtained at the column top under the conditions comprising a vacuum degree of 8 mmHg, a column bottom temperature of 280° C. and no reflux. The yield of the bio-diesel was 83.9 wt %, the acid number was less than 2.0 mgKOH/g, and the fatty acid methyl ester purity was 98.5 wt %. The residual liquid in the column bottom was fed into the molecular rectification device to obtain a light fraction having a relatively high content of monoglyceride at a residual pressure of from 5 to 6 Pa and a heating surface temperature of 190° C. The remaining materials having a high boiling point were fed into a secondary molecular rectification to obtain a light fraction at a residual pressure of 2 Pa and a heating surface temperature of 240-244° C., wherein said light fraction as the raw materials could be recycled to the reactor inlet for the second reaction. The components in the raw materials which could become fatty acid methyl esters were almost converted to the desired product.

Under the same conditions, above waste oil-fat having 14.3 wt % free fatty acid was used as raw materials, and the bio-diesel was produced in a yield of 84.2 wt % and had an acid number of 4.7 mgKOH/g.

Under the same conditions, the bio-diesels were produced in yields of 69 wt % and 76 wt % when a soybean oil and rapeseed oil were used as raw materials respectively.

Example 4

A waste fat-oil having 50 wt % free fatty acid was mixed with the rapeseed oil in comparison example 2 in a mixing ratio of 0.2:1. The mixture was continuously fed into a tubular reactor at an oil liquid hourly space velocity of 1.2 $h^{-1}$ and methanol:oil molar ratio of 6. The reaction temperature was 272° C. and the pressure was 7.2 MPa. The crude product flowing out from the reactor was then depressurized to 0.1-0.13 MPa, then the liquid was entered into a fiber bundle separator at a temperature of 30° C. and a liquid liquid hourly space velocity of 5 $h^{-1}$ to separate out an ester phase and a glycerol phase. The ester phase and glycerol phase were fed into the respective flash columns to remove methanol at a temperature less than 150° C., and recycle and reuse the methanol. After methanol was evaporated, the glycerol was separated and the mixed ester was fed into a film evaporator to evaporate a bio-diesel at a vacuum degree of 8 mmHg and a temperature of 252° C. The yield of the bio-diesel was 93 wt %, the acid number was 4.2 mgKOH/g, and the fatty acid methyl ester purity was 97.3 wt %. The residual liquid in the column bottom was recycled as raw materials to a reactor inlet for a second reaction. The components in the raw materials, which could become fatty acid methyl esters, were almost converted to the desired product.

Under the same conditions, the bio-diesel was produced in a yield of 90 wt % when above waste oil-fat was used as raw materials.

Example 5

A raw rapeseed oil having 29.5 wt % free fatty acid was mixed with the rapeseed oil in comparison example 2 in a mixing ratio of 40:1. The mixture was continuously fed into a tubular reactor at an oil liquid hourly space velocity of 1.2 $h^{-1}$ and methanol:oil molar ratio of 6. The reaction temperature was 272° C. and the pressure was 9.5 MPa. The crude product flowing out from the reactor was depressurized, and then stood for deposition to separate out a mixed ester phase and glycerol phase. The mixed ester phase and glycerol phase were fed into the respective flash columns to continuously flash evaporate methanol respectively at a temperature less than 150° C. The mixed ester phase in which methanol had been evaporated was fed into a vacuum rectification column to evaporate a bio-diesel at the column top at a vacuum degree of 8 mmHg, a column bottom temperature of 252-255° C. and a reflux ratio of 1:1. The yield of the bio-diesel was 86 wt %, and the fatty acid methyl ester purity was up to 99.5 wt %. The residual liquid in the column bottom was fed into a molecular rectification device to evaporate a light fraction at a residual pressure of 1 Pa and a heating surface temperature of 250° C. Said light fraction might be recycled as raw materials to a reactor inlet for a second reaction. The components in the raw materials, which could become fatty acid methyl esters, were almost converted to the product.

Example 6

As raw materials, a cotton seed oil having 5 wt % non-saponifiable matters and 15 wt % free fatty acid, in which 10 wt % oleic acid was added, was continuously fed into a tubular reactor at an oil liquid hourly space velocity of 1.2 $h^{-1}$ and methanol:oil molar ratio of 4.5. The reaction temperature was 272° C. and the pressure was 8 MPa. Methanol and glycerol were separated from the raw product of reaction, which then was vacuum-rectified to evaporate the bio-diesel. The yield of the bio-diesel was 91.3 wt %, and the acid number of the bio-diesel was 3.5 mgKOH/g, and the fatty acid methyl ester had a purity of 97.7 wt %.

The residual liquid in the bottom of the rectification column contained fatty acid methyl ester, monoglyceride, and diglyceride, could be recycled as raw materials to a reactor inlet, and reused after being mixed with fresh raw materials.

Example 7

As raw materials, a waste oil-fat having 4.5 wt % free fatty acid and 1.2 wt % non-saponifiable matters, in which 20 wt % oleic acid was added, was continuously fed into a tubular reactor at an oil liquid hourly space velocity of 1.2 h$^{-1}$ and methanol:oil molar ratio of 5. The reaction temperature was 272° C. and the pressure was 7.4 MPa. The crude product flowing out from the reactor was depressurized, and then fed into a rectification column to remove methanol at a temperature less than 150° C., and recycle and reuse the methanol. The remaining materials were stood for deposition to separate out an ester phase and glycerol phase. The ester phase was fed into a vacuum rectification column to evaporate a bio-diesel at the column top at a vacuum degree of 8 mmHg, a column bottom temperature of 251-255° C. and a reflux ratio of 1:1. The yield of the bio-diesel was 78 wt %. The residual liquid in the column bottom was fed into a molecular rectification device to evaporate a light fraction at a residual pressure of 1 Pa and a heating surface temperature of 250° C. Said light fraction might be recycled as raw materials to a reactor inlet for a second reaction. The components in the raw materials, which could become fatty acid methyl esters, were almost converted to the product.

When the above same raw materials, reaction conditions and separation steps were applied, except for no addition of oleic acid during the reaction, a bio-diesel yield of 45.9 wt % was resulted.

Example 8

As raw materials, a palm oil having 0.35 wt % free fatty acid, in which 15 wt % oleic acid was added, was continuously fed into a tubular reactor at an oil liquid hourly space velocity of 1.2 h$^{-1}$ and methanol:oil molar ratio of 8. The reaction temperature was 272° C. and the pressure was 8 MPa. The crude product flowing out from the reactor was depressurized to 0.1-0.13 MPa, and then fed into a fiber bed containing fiber bundles to separate out a mixed ester phase and glycerol phase at a temperature of 40° C. and a liquid liquid hourly space velocity of 7 h$^{-1}$. The mixed ester phase was fed into a rectification column to remove the methanol at a temperature less than 150° C. and recycle and reuse the methanol. The remaining materials were fed into a fiber bed containing fiber bundles to separate out glycerol at a temperature of 40° C. and a liquid hourly space velocity of 7 h$^{-1}$. The ester phase was vacuum-rectified at a vacuum degree of 5 mmHg and a column bottom temperature of 235-240° C. The yield of the bio-diesel was 69.6 wt %.

The residual liquid in the bottom of the distillation column contained fatty acid methyl ester, monoglyceride, and diglyceride, could be recycled as raw materials to a reactor inlet, and reused after being mixed with fresh raw materials. The components in the raw materials, which could become fatty acid methyl esters, were almost converted to the product.

When the above same raw materials, reaction conditions and separation steps were applied, except for no addition of oleic acid during the reaction, a bio-diesel yield of 34.9 wt % was resulted.

Example 9

As raw materials, a soybean oil having 2.5 wt % free fatty acid, in which 3 wt % free unsaturated $C_{16}$ fatty acid was added, was continuously fed into a tubular reactor at an oil liquid hourly space velocity of 1.2 h$^{-1}$ and methanol:oil molar ratio of 15. The reaction temperature was 300° C. and the pressure was 9 MPa. The crude product, from which methanol and glycerol had been separated, was vacuum-rectified to produce the bio-diesel in a yield of 72 wt %.

The residual liquid in the bottom of the rectification column contained fatty acid methyl ester, monoglyceride, and diglyceride, could be recycled as raw materials to a reactor inlet, and reused after being mixed with fresh raw materials.

When the above same raw materials, reaction conditions and separation steps were applied, except for no addition of free unsaturated $C_{16}$ fatty acid during the reaction, a bio-diesel yield of 55 wt % was resulted.

It should be understood that various changes and modifications to the present invention can be made by those skilled in the art without departing the inventive scope so as to be applicable for the various objectives and conditions. Therefore, these changes and modifications should be suitably and reasonably encompassed in all the equivalent scopes of the accompanying claims.

What is claimed is:

1. A process for preparing a bio-diesel, comprising the steps of, in the presence of an additional free fatty acid source, reacting a raw oil-fat with $C_1$-$C_6$ monohydric alcohol in a reactor, and separating fatty acid esters from the reacted materials, so as to produce the bio-diesel, wherein the amount of the free fatty acid in the free fatty acid source ranges from 2-100 wt % and is higher than the amount of the free fatty acid in the raw fat-oil.

2. The process according to claim 1, characterized in that said free fatty acid source is a free fatty acid.

3. The process according to claim 2, characterized in that said free fatty acid is a $C_{10}$-$C_{24}$ saturated or unsaturated fatty acid.

4. The process according to claim 2, characterized in that said free fatty acid is a $C_{12}$-$C_{18}$ unsaturated fatty acid.

5. The process according to claim 2, characterized in that said free fatty acid is oleic acid.

6. The process according to claim 2, characterized in that said free fatty acid is present in an amount of 1-50 wt %, relative to the weight of the raw oil-fat.

7. The process according to claim 2, characterized in that said free fatty acid is present in an amount of 2-40 wt %, relative to the weight of the raw oil-fat.

8. The process according to claim 1, characterized in that said free fatty acid source is an oil-fat having a high acid number wherein the amount of the free fatty acid is in an amount of more than 2 wt %.

9. The process according to claim 8, characterized in that the amount of the free fatty acid in said oil-fat having a high acid number is 5 to <100 wt %.

10. The process according to claim 8, characterized in that the amount of the free fatty acid in said oil-fat having a high acid number is 10 to 60 wt %.

11. The process according to claim 8, characterized in that said oil-fat having a high acid number is a raw oil or waste oil-fat.

12. The process according to claim 8, characterized in that the weight ratio between the raw oil-fat and the oil-fat having a high acid number ranges from 1:0.02 to 50.

13. The process according to claim 8, characterized in that the weight ratio between the raw oil-fat and the oil-fat having a high acid number ranges from 1:0.04 to 20.

14. The process according to claim 8, characterized in that the weight ratio between the raw oil-fat and the oil-fat having a high acid number ranges from 1:0.06 to 10.

15. The process according to claim 1, characterized in that the amount of the free fatty acid in said raw oil-fat is less than 50 wt %.

16. The process according to claim 15, characterized in that the amount of the free fatty acid in said raw oil-fat is less than 30 wt %.

17. The process according to claim 16, characterized in that the amount of the free fatty acid in said raw oil-fat is less than 20 wt %.

18. The process according to claim 1, characterized in that said raw oil-fat comprises palm oil.

19. The process according to claim 1, characterized in that said raw oil-fat is a waste oil-fat.

20. The process according to claim 1, characterized in that said $C_1$-$C_6$ monohydric alcohol is methanol or ethanol.

21. The process according to claim 1, characterized in that the molar ratio of $C_1$-$C_6$ monohydric alcohol to the raw oil-fat ranges from 3 to 60:1.

22. The process according to claim 1, characterized in that the molar ratio of $C_1$-$C_6$ monohydric alcohol to the raw oil-fat ranges from 4 to 12:1.

23. The process according to claim 1, characterized in that the reaction between the raw oil-fat and $C_1$-$C_6$ monohydric alcohol in the presence of an additional free fatty acid source is carried out under the condition that an alkaline compound is used as a catalyst.

24. The process according to claim 1, characterized in that said reactor is a tubular reactor.

25. The process according to claim 1, characterized in that the reaction temperature ranges from 200 to 320° C.

26. The process according to claim 1, characterized in that the reaction temperature ranges from 230 to 280° C.

27. The process according to claim 1, characterized in that the reaction pressure ranges from 5 to 12 MPa.

28. The process according to claim 1, characterized in that the reaction pressure ranges from 5 to 10 MPa.

29. The process according to claim 1, characterized in that the reaction pressure ranges from 5 to 7.5 MPa.

30. The process according to claim 1, characterized in that the total liquid hourly space velocity of the raw oil-fat and additional free fatty acid source ranges from 0.1 to 10 $h^{-1}$.

31. The process according to claim 1, characterized in that the total liquid hourly space velocity of the raw oil-fat and additional free fatty acid source ranges from 0.5 to 6 $h^{-1}$.

32. The process according to claim 1, characterized in that the separation of fatty acid esters comprises the steps of (A) separating the mixed ester phase and the glycerol phase formed in the reacted materials, and subsequently evaporating monohydric alcohols respectively from said mixed ester phase and optionally from the glycerol phase, or evaporating monohydric alcohols from the reacted materials before separating the mixed ester phase and the glycerol phase formed in the reacted materials; and (B) distilling or rectifying the mixed ester phase processed in step (A), or water-washing the mixed ester phase processed in step (A) and separating the ester phase formed after washing from the aqueous phase and collecting said ester phase, to obtain fatty acid esters, and optionally distilling the glycerol phase processed in step (A) to obtain glycerol.

33. The process according to claim 32, characterized in that the monohydric alcohol is evaporated in step (A) by flash distillation or rectification under the condition that the temperature at the column bottom is less than 150° C.

34. The process according to claim 32, characterized in that, in step (A), the separation between the mixed ester phase and the glycerol phase is carried out by deposition or via a fiber bundle separator.

35. The process according to claim 34, characterized in that said fiber bundle separator consists of a separating cylinder and a receiving tank, wherein the separating cylinder is furnished with fiber bundles consisting of stainless steel wires, and the separation between the mixed ester phase and the glycerol phase is carried out by passing them through the separating cylinder and then feeding into the receiving tank for stratification.

36. The process according to claim 32, characterized in that, during the washing process in step (B), an alkaline matter is added into the washing water.

37. The process according to claim 32, characterized in further comprising step (C): evaporating monoglycerides and diglycerides from the mixed ester phase residues distilled or rectified in step (B) by using a primary molecular rectification, or evaporating and separating monoglycerides and diglycerides from the mixed ester phase residues distilled or rectified in step (B) by using a secondary molecular rectification, with or without a second reaction.

\* \* \* \* \*